(12) United States Patent
McCanless et al.

(10) Patent No.: US 11,918,348 B2
(45) Date of Patent: Mar. 5, 2024

(54) MEDICAL DEVICES HAVING A DYNAMIC SURFACE PROFILE AND METHODS FOR PRODUCTION AND USE THEREOF

(71) Applicant: Abbott Diabetes Care Inc., Alameda, CA (US)

(72) Inventors: Jonathan McCanless, Oakland, CA (US); Hyun Brian Cho, Berkeley, CA (US); Benjamin Feldman, Berkeley, CA (US); Frank David Fujimoto, Fremont, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 200 days.

(21) Appl. No.: 16/205,792

(22) Filed: Nov. 30, 2018

(65) Prior Publication Data
US 2019/0167166 A1    Jun. 6, 2019

Related U.S. Application Data

(60) Provisional application No. 62/594,700, filed on Dec. 5, 2017.

(51) Int. Cl.
*A61B 5/145* (2006.01)
*A61B 5/00* (2006.01)

(52) U.S. Cl.
CPC ...... *A61B 5/14503* (2013.01); *A61B 5/14532* (2013.01); *A61B 5/14546* (2013.01);
(Continued)

(58) Field of Classification Search
CPC ............ A61B 5/14503; A61B 5/14532; A61B 5/14546; A61B 5/4839; A61B 5/6802;
(Continued)

(56) References Cited

U.S. PATENT DOCUMENTS 6,063,029 A * 5/2000 Saita .................. A61B 10/0035
600/309
9,779,352 B1 * 10/2017 Hyde .................. G06K 19/041
(Continued)

OTHER PUBLICATIONS

Hardy, John G., et al., "Hydrogel-Forming Microneedle Arrays Made from Light-Responsive Materials for On-Demand Transdermal Drug Delivery," Molecular Pharmaceutics, vol. 13, No. 3, Feb. 8, 2016, pp. 907-914, XP055554992, US ISSN: 1543-8384, DOI: 10.1021/acs.molpharmaceut.5b00807.
(Continued)

*Primary Examiner* — Alex M Valvis
*Assistant Examiner* — Chanel J Jhin
(74) *Attorney, Agent, or Firm* — Sterne, Kessler, Goldstein & Fox P.L.L.C.

(57) ABSTRACT

Medical devices configured for in vivo assays of one or more analytes can sometimes be problematic if left inserted in a tissue, such as skin, for an extended time. Certain medical device surface profiles may aid in alleviating this issue. Accordingly, medical devices may comprise a base surface having a tissue-facing surface profile defined thereon, and a sensor extending through the base surface and at least a portion of the tissue-facing surface profile. The tissue-facing surface profile deviates from the base surface, and the tissue-facing surface profile is also configured to undergo a change in shape, hardness, or a combination thereof after contacting a tissue for a length of time. A dynamic material may be present in at least a portion of the tissue-facing surface profile.

19 Claims, 8 Drawing Sheets

(52) U.S. Cl.
CPC .......... *A61B 5/4839* (2013.01); *A61B 5/6802* (2013.01); *A61B 5/6849* (2013.01); *A61B 5/0002* (2013.01); *A61B 2560/0406* (2013.01); *A61B 2562/02* (2013.01); *A61B 2562/12* (2013.01); *A61B 2562/164* (2013.01)

(58) Field of Classification Search
CPC ................ A61B 5/6849; A61B 5/0002; A61B 2560/0406; A61B 2562/02; A61B 2562/12; A61B 2562/164
USPC ......................................................... 600/309
See application file for complete search history.

(56) References Cited

U.S. PATENT DOCUMENTS

| | | | | |
|---|---|---|---|---|
| 9,974,471 | B1* | 5/2018 | Kam | A61B 5/14514 |
| 2004/0249254 | A1* | 12/2004 | Racchini | A61B 5/150412 |
| | | | | 600/347 |
| 2008/0009692 | A1* | 1/2008 | Stafford | A61B 5/0022 |
| | | | | 600/345 |
| 2008/0194988 | A1* | 8/2008 | Nakamura | A61B 5/150412 |
| | | | | 600/583 |
| 2014/0213866 | A1* | 7/2014 | Simpson | A61B 17/3468 |
| | | | | 600/345 |
| 2014/0275907 | A1* | 9/2014 | Feldman | A61B 5/14532 |
| | | | | 600/365 |
| 2017/0027514 | A1* | 2/2017 | Biederman | A61B 5/1451 |
| 2017/0188912 | A1* | 7/2017 | Halac | A61B 5/14532 |

OTHER PUBLICATIONS

Wang, Min et al., "Recent advances in the design of polymeric microneedles for transdermal drug delivery and biosensing," Lab on a Chip, vol. 17, No. 8, Jan. 1, 2017, pp. 1373-1387, XP055554994, ISSN: 1473-0197, DOI: 10.1039/C7LC00016B.
International Search Report and Written Opinion received in corresponding PCT Application No. PCT/US2018/063263, search completed Feb. 12, 2019, dated Feb. 20, 2019.

* cited by examiner

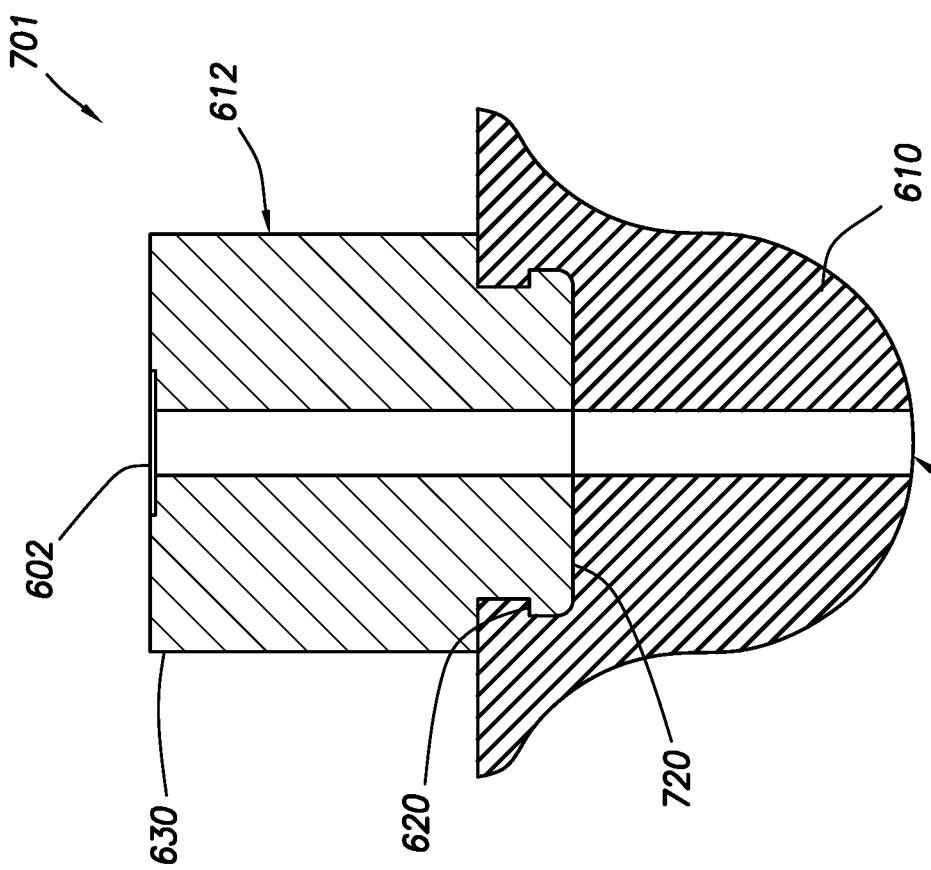
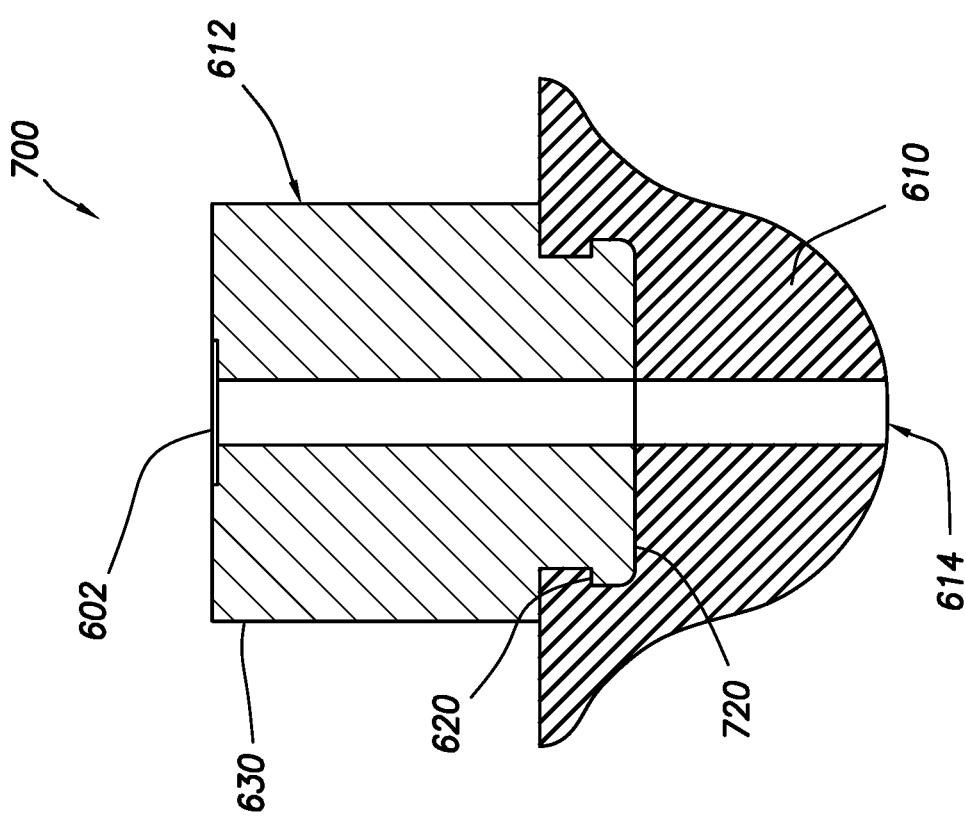

MEDICAL DEVICES HAVING A DYNAMIC SURFACE PROFILE AND METHODS FOR PRODUCTION AND USE THEREOF

CROSS-REFERENCE TO RELATED APPLICATIONS

This application claims priority to U.S. provisional application 62/594,700, filed on Dec. 5, 2017.

STATEMENT REGARDING FEDERALLY SPONSORED RESEARCH OR DEVELOPMENT

Not applicable.

BACKGROUND

The detection of various analytes within an individual can sometimes be vital for monitoring the condition of their health. Deviation from normal analyte levels can often be indicative of a number of physiological conditions. Glucose monitoring, for example, can be particularly important to detect irregular analyte levels in diabetic individuals. By monitoring glucose levels with sufficient regularity, a diabetic individual may be able to take corrective action (e.g., by injecting insulin to lower glucose levels or by eating to raise glucose levels) before significant physiological harm occurs. Other analytes commonly subject to physiological dysregulation that may similarly be desirable to monitor include, but are not limited to, lactate, oxygen, pH, A1c, ketones, drug levels, and the like.

Analyte monitoring in an individual may take place periodically or continuously over a period of time. Periodic analyte monitoring may take place by withdrawing a sample of bodily fluid, such as blood, at set time intervals and analyzing ex vivo. Continuous analyte monitoring may be conducted using one or more sensors that remain implanted within a tissue of an individual, such as dermally, subcutaneously or intravenously, such that analyses are conducted in vivo. Implanted sensors may collect analyte data continuously or sporadically, depending on an individual's particular health needs or measured analyte levels.

Periodic, ex vivo analyte monitoring can be sufficient to determine the physiological condition of many individuals. However, ex vivo analyte monitoring may be inconvenient or painful for some individuals. Moreover, there is no way to recover lost data if a measurement is not obtained at an appropriate time.

Continuous analyte monitoring may be a more desirable approach for individuals having severe analyte dysregulation and/or rapidly fluctuating analyte levels, although it can also be beneficial for other individuals as well. While continuous analyte monitoring with an implanted sensor can be advantageous, there are challenges associated with these types of measurements. Intravenous analyte sensors have the advantage of providing analyte concentrations directly from blood, but they are invasive and can sometimes be painful for an individual to wear for an extended period. Subcutaneous and dermal analyte sensors can often be less painful to wear than are intravenous analyte sensors, but they too can cause undesirable site discomfort and/or tissue trauma where contact with a skin surface occurs, particularly upon extended wear. The immunological response resulting from tissue trauma can, in some instances, skew local analyte levels away from their true values. For example, in the case of glucose monitoring, trauma at the sensor implantation site may lead to a heightened and localized over-consumption of glucose as a cellular metabolic response.

An analyte sensor may be mounted within a housing having a surface profile that is configured to contact a tissue surface in proximity to the site of sensor insertion. The surface profile may further impact various aspects of the sensing process. For example, a surface protrusion may increase the volumetric flow of blood (perfusion) in proximity to the site of sensor insertion, which may increase the accuracy of analyte detection. Without being bound by any theory or mechanism, the protrusion may increase perfusion by applying a pressure profile to the skin, which results in a biological response of pressure-induced vasodilation. A designed pressure profile may result in a patterning of high and low perfusion areas across the skin. Recesses or depressions may similarly be incorporated within a surface profile to alter perfusion over a given skin surface as well. In addition to improving the accuracy of analyte detection, increased perfusion may additionally improve tissue grafting; transdermal, systemic or localized drug delivery; wound healing, and the like.

Due to its dense capillary bed, the dermis may be an especially appealing target for modification by interaction with a designed surface profile, particularly to impact perfusion in an advantageous manner. In addition to impacting perfusion, the surface profile morphology may further influence other various factors associated with the sensing process. Harder, less compliant materials within the surface profile may increase the success rate for sensor insertion and aid in properly localizing the sensor in vivo (e.g., by decreasing the extent of needle and/or sensor bowing or misalignment). Unfortunately, prolonged contact of dermal or epidermal tissue with a hard material following sensor insertion may result in bruising, erythema, discomfort, or other irritation that may provoke a physiological response leading to inaccurate measurement of analyte levels and/or decrease an individual's enjoyment of wearing the sensor. Softer, more compliant materials are less capable of providing the sensor insertion and localization benefits described above.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIGS. 6A, 6B, 7A and 7B show cross-sectional diagrams of surface profiles incorporating a dynamic material in an exterior layer upon a core material.

DETAILED DESCRIPTION

Figure 1:
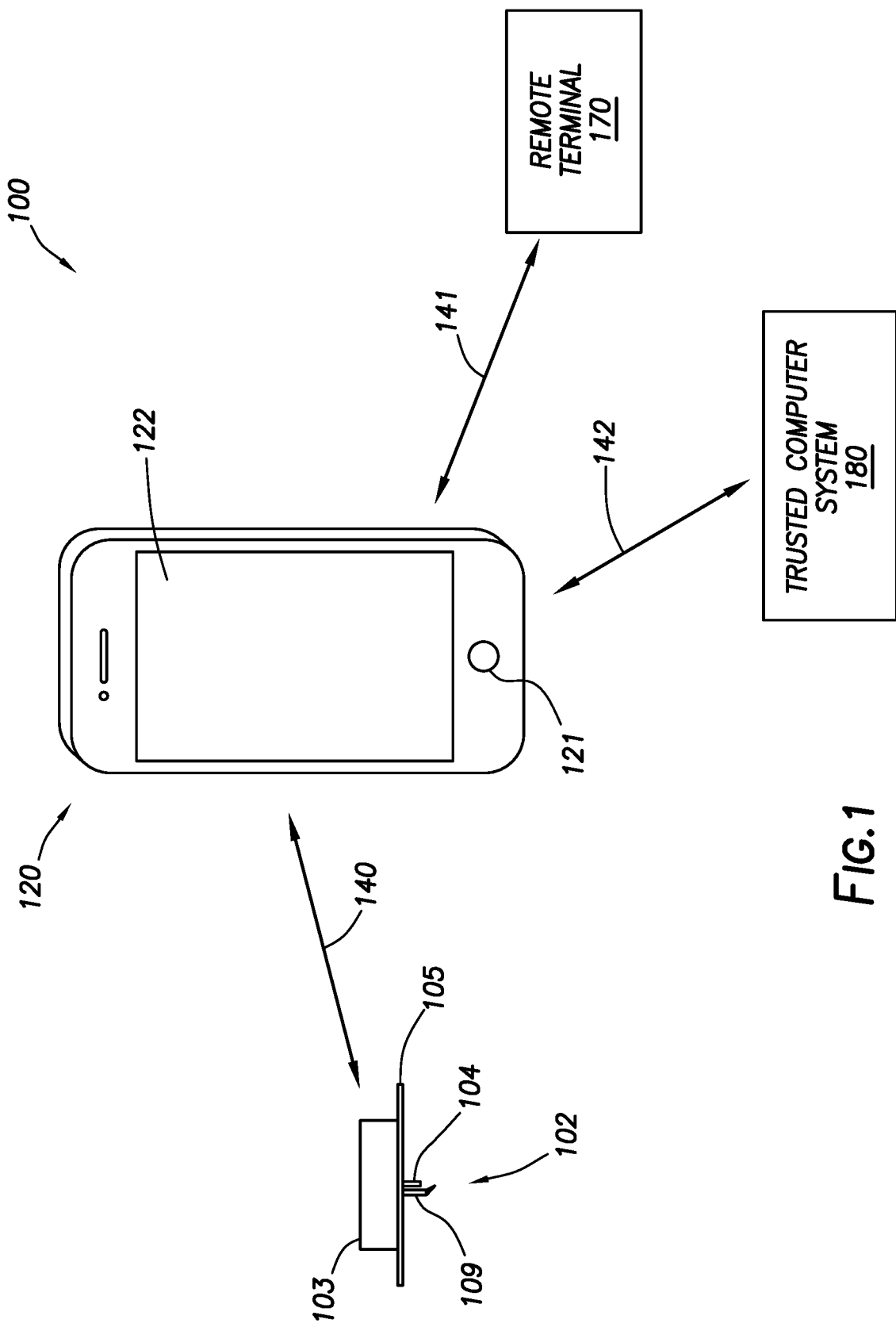
FIG. 1 shows a diagram of an illustrative analyte monitoring system that may incorporate one or more features of the present disclosure.

The present disclosure generally describes sensors suitable for in vivo use and, more specifically, medical devices and methods for their production and use, in which a dynamic surface profile is provided proximate to a site of sensor insertion.

As discussed above, it can be desirable for a surface profile, such as a protrusion, to contact a tissue proximate to an insertion site of a sensor. Pressure applied to the tissue via the surface profile may improve perfusion, as well as provide other benefits in some cases. Hard, less compliant materials are often used for defining a surface profile, since hard materials may aid in promoting proper sensor insertion and localization within a tissue. However, prolonged contact of hard materials with a tissue may lead to complications such as bruising and erythema, which may make the sensor uncomfortable or undesirable for an individual to wear. In certain instances, open wounds and infections may arise from prolonged contact with hard materials. While softer, more compliant materials may improve user comfort, they are often unable to provide the sensor insertion and localization benefits afforded by harder materials.

Given the above issues, it was discovered to be desirable to lower the amount of time a tissue remains in contact with hard materials of a surface profile following sensor insertion, but without prematurely removing the sensor to alleviate contact with the hard materials. Moreover, the benefits of incorporating a hard material within a surface profile to promote proper sensor insertion and localization are appreciated in the present disclosure, rather than exploring simple replacement of a hard material with a soft material. To rectify this seeming disconnect, the present disclosure shows how one or more dynamic materials may be incorporated within at least a portion of a surface profile to allow the advantages of both hard and soft materials to be realized. As used herein, the term "dynamic material" refers to a substance that undergoes a change in shape, hardness, or a combination thereof over time. These changes may arise from a chemical and/or physical change in the dynamic material. In certain embodiments, the dynamic material may undergo softening over time. Particular dynamic materials and conditions for affecting a change in their shape and/or hardness are discussed hereinbelow.

More specifically, the present disclosure shows that by incorporating a softenable dynamic material within a surface profile, the benefits of both hard and soft materials may be realized. Namely, a dynamic material in an initially hard state may promote sensor insertion and localization. Upon softening following sensor insertion, the dynamic material may then promote user comfort and improved performance during extended wear. The transition from a hard state to a softer state may occur over a range of times following exposure to a number of environmental and/or physiological conditions, and particular materials may be chosen depending the anticipated conditions to which the surface profile will be exposed, as well as the desired rate of morphological change. In illustrative embodiments, the change in shape and/or hardness may occur over a range of several minutes to several days, depending upon particular exposure conditions and the chemical identity of the dynamic material, in addition to other factors.

In addition to promoting comfort for a wearer, certain surface profiles of the present disclosure may tend to flatten as the dynamic material transitions to a softer state. Flattening of the surface profile following sensor insertion may expose a larger section of the sensor body, which may facilitate deeper sensor insertion into a tissue and lessen premature sensor pullout and migration issues. Thus, the surface profiles disclosed herein may also prolong sensor lifetime and improve reliability by setting the sensor more securely.

Various surface profile configurations capable of undergoing a change in shape and/or hardness in response to given conditions are described hereinbelow. Advantageously, the surface profiles disclosed herein may be fabricated upon an insert (plug) that may be affixed to a base surface of a medical device. As such, in some instances, the surface profiles of the present disclosure may be readily interchanged upon a common interface in response to the needs of a particular application.

As a still further advantage of the surface profiles disclosed herein, the transition of the dynamic material from a hard state to a softer state may facilitate delivery of a drug substance, biologically active material or other therapeutic agent proximate to the site of sensor insertion. Suitable drug substances and biologically active materials are not considered to be particularly limited, provided that they can be incorporated within the surface profile while the dynamic material is in a hard state and then undergo release once the transition to the softer state occurs. In some instances, drug substances and/or biologically active materials that may alleviate site trauma or promote wearer comfort may be incorporated within the surface profile. The drug substance and/or biologically active materials may be incorporated within a protrusion of the surface profile, according to some embodiments.

In some embodiments, the surface profile concepts disclosed herein may be practiced independently of sensor insertion for delivery of drug substances or other biologically active materials. That is, such drug substances and other biologically active materials may be incorporated within a surface profile of the present disclosure (e.g., within an adhesive drug delivery patch) that is configured to contact a tissue surface and undergo a change in shape and/or hardness over time, but without a physical penetration of the tissue surface occurring.

Before discussing particular surface profile configurations incorporating a dynamic material, a brief overview of conventional surface profiles associated with in vivo sensor use and placement will be provided so that the embodiments of the present disclosure can be better understood. Any of the various surface profiles discussed hereinafter in reference to FIGS. 1-5 can be further modified to incorporate a dynamic material to realize at least some of the features and advantages discussed hereinabove. It should be noted that the relative dimensions of the surface profiles depicted in FIGS. 1-5, as well as those described elsewhere herein, are illustrative in nature and should be considered non-limiting, unless particular surface profile dimensions are mentioned herein. In illustrative, yet non-limiting embodiments, the surface profiles may be incorporated in combination with a dermal sensor. Illustrative dermal sensors and surface profiles that may be modified to incorporate the concepts of the present disclosure are described in commonly owned U.S. Patent Application Publication 2017/0196487 and commonly owned U.S. Pat. No. 9,668,686, each of which is incorporated herein by reference in its entirety.

FIG. 1 shows a diagram of an illustrative analyte monitoring system that may incorporate one or more features of the present disclosure. As shown, analyte monitoring system 100 includes sensor control device 102 and reader device 120 that are configured to communicate with one another over a local communication path or link 140, which may be wired or wireless, uni- or bi-directional, and encrypted or non-encrypted. Reader device 120 may also be in communication with remote terminal 170 and/or trusted computer system 180 via communication path(s)/link(s) 141 and/or 142, respectively, which also may be wired or wireless, uni- or bi-directional, and encrypted or non-encrypted. Any suitable electronic communication protocol may be used for each of the local communication paths or links. Reader device 120 may comprise display 122 and optional input component 121.

Sensor control device 102 includes sensor housing 103, which may include circuitry and a power source for operating sensor 104. Sensor 104 protrudes from sensor housing 103 and extends through surface profile 105. Surface profile 105 may exhibit a deviation in planarity with respect to a base surface, as discussed hereinafter. Surface profile 105 may be a tissue-facing profile that is configured to contact and adhere to a tissue, such as the epidermal layer of the skin, for example. In some illustrative embodiments, at least a portion of surface profile 105 may comprise an adhesive to promote adhesion to a suitable tissue. Suitable adhesives will be familiar to one having ordinary skill in the art.

Sensor 104 is adapted to be at least partially inserted into a tissue of interest, such as the dermal layer of the skin. Sensor 104 may comprise a sensor tail of sufficient length for insertion to a desired depth in a given tissue. Surface profile 105 may further impact the depth to which sensor 104 becomes inserted in the tissue, as discussed in further detail hereinbelow. One or more analyte levels may be determined using sensor 104 and undergo communication to reader device 120, according to one or more embodiments. The analyte may be monitored in any biological fluid such as dermal fluid, plasma, blood, lymph, or the like. Analytes that may be monitored are not considered to be particularly limited. In certain embodiments, the analyte may be glucose. Other analytes of interest with respect to human physiology may include, for example, lactate, oxygen, pH, A1c, ketones, drug levels, and the like. Both single analytes and any combination of the foregoing analytes may be assayed.

An introducer may be present to promote introduction of sensor 104 into a tissue. In illustrative embodiments, the introducer may comprise needle 109, as shown in FIG. 1. Although FIG. 1 has shown needle 109 as an illustrative introducer, it is to be recognized that other types of introducers, such as sheaths or blades, may be present in alternative embodiments. More specifically, needle 109 may reside in proximity to sensor 104. When present, needle 109 may facilitate insertion of sensor 104 into a tissue by opening an access pathway for sensor 104 to follow. For example, needle 109 may facilitate penetration of the epidermis as an access pathway to the dermis to allow implantation of sensor 104 to take place, according to one or more embodiments. In illustrative embodiments, needle 109 may be solid or hollow, beveled or non-beveled, and/or circular or non-circular in cross-section. In more particular embodiments, needle 109 may be comparable in cross-sectional diameter and/or tip design to an acupuncture needle, which may have a cross-sectional diameter of about 250 microns. It is to be recognized, however, that needle 109 may have a larger or smaller cross-sectional diameter if needed for particular applications. In alternative embodiments, needle 109 or similar introducers may be absent, provided sensor 104 is able to satisfactorily penetrate a tissue to establish communication with a bodily fluid of interest.

In some embodiments, a tip of needle 109 may be angled over the terminus of sensor 104, such that needle 109 penetrates a tissue first and opens an access pathway for sensor 104. In other illustrative embodiments, sensor 104 may reside within a lumen or groove of needle 109, with needle 109 similarly opening an access pathway for sensor 104.

It is to be recognized that analyte monitoring system 100 may comprise additional features and functionality that are not necessarily described herein in the interest of brevity. Accordingly, the foregoing description of analyte monitoring system 100 should be considered illustrative and non-limiting in nature.

Further details concerning surface profile 105 are provided hereinafter in reference to FIGS. 2-8, each of which shows a deviation of surface profile 105 from a base surface of housing 103. It is to be emphasized that the depicted configurations are illustrative in nature and should be considered non-limiting. Various features such as surface profile widths, heights, depths, aspect ratios, patterning, and the like may vary from that depicted. Common reference characters are used herein to annotate elements previously described hereinabove. In the interest of brevity, such elements are not described again in detail unless needed to further elaborate upon a particular surface profile configuration. In certain instances, sensor 104 and/or needle 109 or a similar introducer are not shown in FIGS. 2-8 in the interest of clarity, but it is to be appreciated that these elements may be disposed in a manner similar to that shown in FIG. 1.

More specifically, sensor 104 may extend through at least a portion of surface profile 105 according to one or more embodiments. According to various embodiments, surface profile 105 may be a tissue-facing surface profile that is configured to contact a tissue of interest when sensor 104 is implanted therein. In still more specific embodiments, surface profile 105 may be skin-facing surface.

As indicated above, surface profile 105 may deviate from a base surface of housing 103. In some embodiments, the base surface may be planar, and surface profile 105 may represent a deviation in planarity with respect to the base surface. Non-planar base surfaces also lie within the scope of the present disclosure, and surface profile 105 may similarly deviate from such base surfaces as well. The deviation of surface profile 105 may be either concave or convex in nature, such that depressions or protrusions are defined in the base surface. In addition, in some embodiments, surface profile 105 may comprise both concave and convex portions. In still more specific embodiments, surface profile 105 may comprise one or more protrusions extending from the base surface of housing 103. Optionally, a protrusion defining surface profile 105 may comprise both a convex portion and a concave portion.

Figure 2:
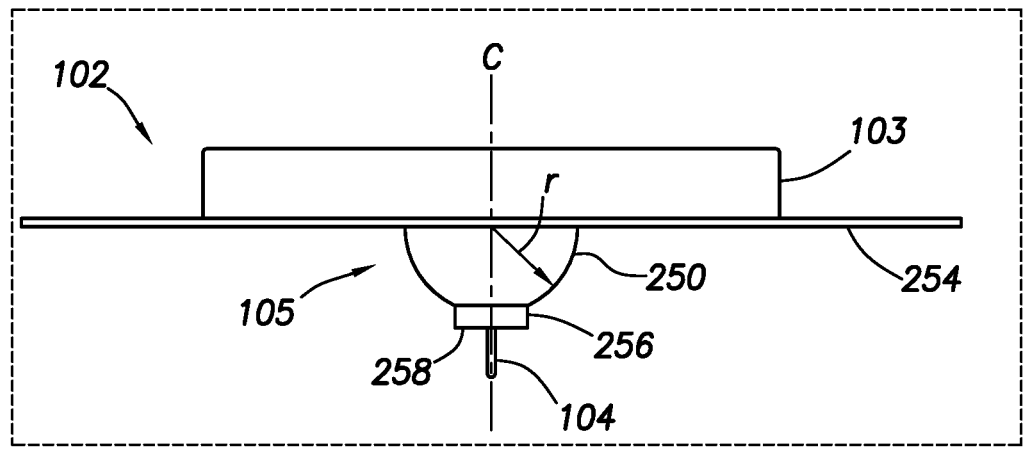
FIG. 2 shows a diagram of a surface profile configuration that is generally hemispherical in shape.

FIG. 2 shows a diagram in which the configuration of surface profile 105 is generally hemispherical in shape. More specifically, protrusion 250 is generally hemispherical in shape and is defined by radius r. Radius r represents the distance measured from base surface 254 at centerline C to the exterior surface of protrusion 250. As will be appreciated by one having ordinary skill in the art, slight radial deviations may be present while still maintaining a generally hemispherical shape of protrusion 250. Accordingly, the term "generally hemispherical," as used herein, refers to both true hemispherical shapes having a constant radius and pseudo-hemispherical shapes exhibiting a slight radial deviation (e.g., radial deviation values of less than about 20%) at various locations upon the exterior surface. In some embodiments, a pseudo-hemispherical surface profile may exhibit a radial deviation of less than about 5%.

As further shown in FIG. 2, protrusion 250 may optionally be truncated distal to base surface 254. More specifically, protrusion 250 may optionally comprise terminus 256 having substantially planar distal face 258, through which sensor 104 may extend. Terminus 256 may alternately be non-planar in nature at distal face 258. It is to be recognized that distal face 258 may likewise exhibit slight and unavoidable deviation from planarity while still being considered substantially planar (e.g., due to manufacturing limitations and the like). Non-planarity in distal face 258 is also possible as well. Furthermore, distal face 258 may be cylindrical in shape (footprint), as depicted in FIG. 2, as well as a variety of other shapes, such as ovular, square, rectangular, polygonal, hemispherical, and the like. Distal face 258 may comprise an irregular or non-planar geometric form as well, according to some embodiments.

Figure 3:
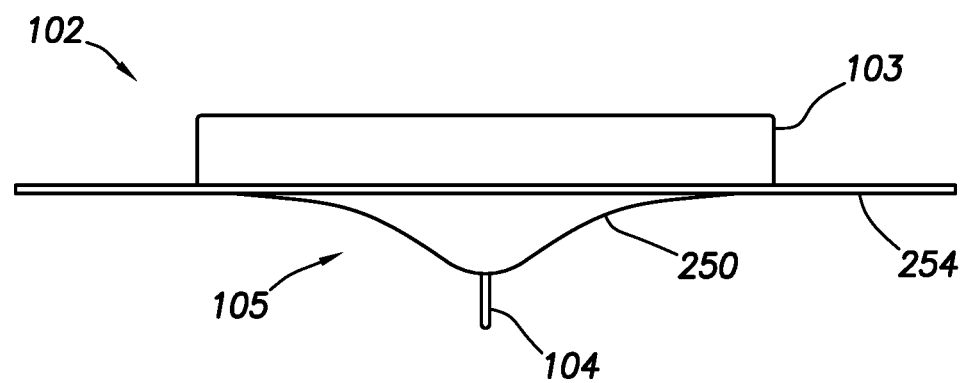
FIG. 3 shows a diagram of a surface profile configuration having a cross-section similar in shape to a Gaussian distribution. The cross-section contains two inflection points, such that both concave and convex portions are defined in the surface profile.

FIG. 3 shows a diagram in which the configuration of surface profile 105 has a cross-section similar in shape to a Gaussian distribution or related wave-like shape. In this case, surface profile 105 contains two inflection points, such that both concave and convex portions are defined. Although the depicted configuration is substantially symmetrical, surface profile 105 may be asymmetrical in shape in alternative embodiments. Repeating, wave-like patterns for surface profile 105, such as a sinusoidal pattern, are also possible in some embodiments. Moreover, the depicted height and width in FIG. 3 should not be considered limiting. The surface profile configuration shown in FIG. 3 lacks terminus 256 and distal face 258, similar to those shown in FIG. 2, but it is to be appreciated that these features may likewise be present in some embodiments.

Figure 4:
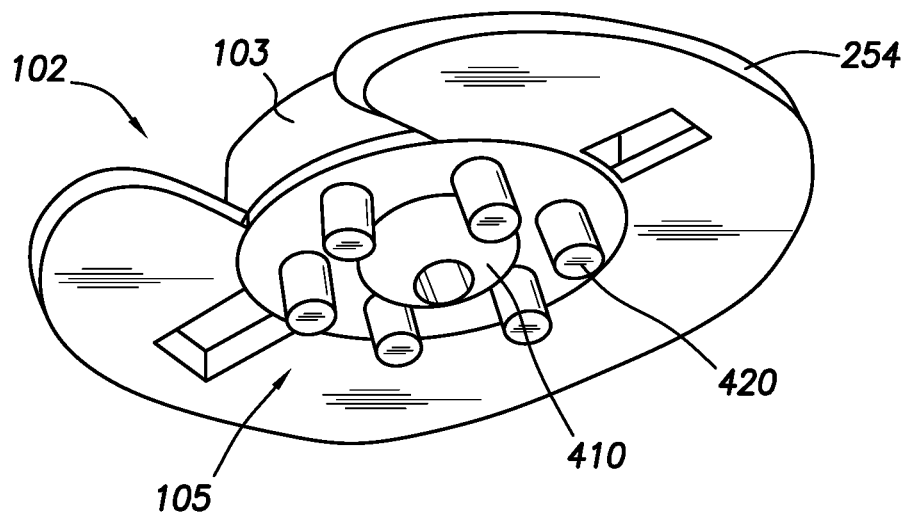
FIG. 4 shows a diagram of a surface profile configuration in which multiple protrusions extend from a base surface.

FIG. 4 shows a diagram in which the configuration of surface profile 105 includes multiple protrusions extending from base surface 254. In particular, the configuration of surface profile 105 in FIG. 4 contains hemispherical or pseudo-hemispherical central protrusion 410 and columnar secondary protrusions 420 spaced radially around central protrusion 410. Although FIG. 4 has shown six secondary protrusions 420, it is to be recognized that any number may be present, and their spacing may be regular or irregular. Accordingly, the particular configuration shown in FIG. 4 should not be considered limiting. When no secondary protrusions 420 are present, the configuration of FIG. 4 may be similar to that of the hemispherical configuration of FIG. 2 when terminus 256 is optionally omitted. Moreover, secondary protrusions 420 need not necessarily by columnar in shape. For example, secondary protrusions 420 may have a square, rectangular, ovular or polygonal base instead of the depicted circular base. Furthermore, in some embodiments, secondary protrusions 420 may be hemispherical, pseudo-hemispherical, or have a cross-section that is similar in shape to a Gaussian distribution or like distribution, or secondary protrusions 420 may be wave-like. Secondary protrusions 420 may also have a rounded terminus, pointed terminus, a flat terminus, an angled terminus, or a non-planar terminus, and secondary protrusions 420 may all have similar lengths or some may have different lengths, according to some embodiments. In still further embodiments, central protrusion 410 may have a cross-section that is similar in shape to a Gaussian distribution or like distribution, instead of the depicted hemispherical shape. Related wave-like patterns for central protrusion 410 are possible as well.

Figure 5:
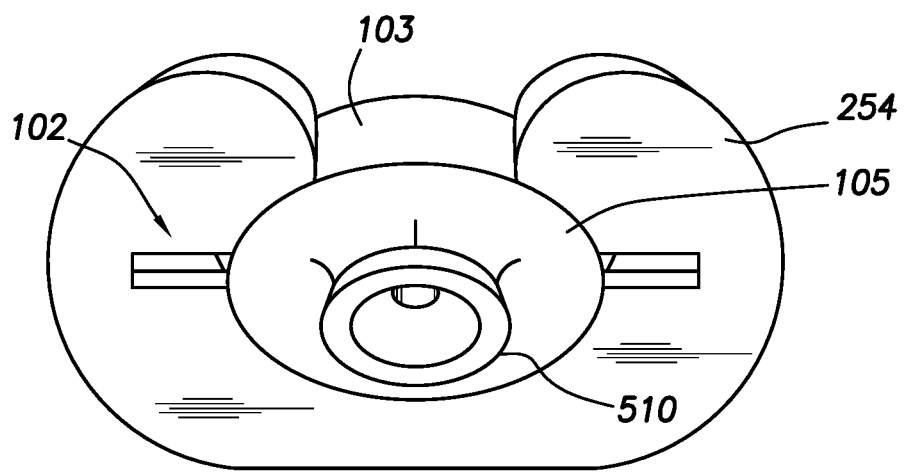
FIG. 5 shows a diagram of a surface profile configuration in which a ring-shaped protrusion extends from a base surface.

FIG. 5 shows a diagram in which the configuration of surface profile 105 includes ring-shaped protrusion 510 extending from base surface 254. As such, surface profile 105 in FIG. 5 includes a concave portion within the interior of ring-shaped protrusion 510. Although FIG. 5 has shown a single ring-shaped protrusion 510, it is to be recognized that multiple ring-shaped protrusions 510 may be present, according to some embodiments. When multiple ring-shaped protrusions 510 are present, they may be concentric or non-concentric with respect to one another. Moreover, ring-shaped protrusions 510 need not necessarily be substantially circular, as depicted. In illustrative embodiments, ring-shaped protrusion 510 may be ovular, square, rectangular, polygonal or irregular in shape, with a concave portion being defined interiorly in each case. Moreover, according to still further embodiments, ring-shaped protrusion 510 may be combined with any of the other surface profile configurations disclosed herein.

According to various embodiments of the present disclosure, a surface profile of a medical device for assaying an analyte may be configured to undergo a change in shape, hardness or a combination thereof after contacting a tissue for a length of time. In more particular embodiments, surface profiles of the present disclosure may be configured to soften and deform upon prolonged contact with a tissue surface, such as a skin surface. Softening of the surface profile following sensor insertion can help avoid the issues discussed hereinabove that occur during extended contact with a tissue, such as skin. Any of the surface profiles discussed hereinabove may be further modified to undergo a change in shape, hardness or a combination thereof in accordance with the embodiments of the present disclosure. Further examples are also discussed hereinafter.

Accordingly, in various embodiments, the present disclosure describes medical devices comprising: a base surface having a tissue-facing surface profile defined thereon, and a sensor extending through the base surface and at least a portion of the tissue-facing surface profile. The tissue-facing surface profile deviates from the base surface, and the tissue-facing surface profile is configured to undergo a change in shape, hardness, or a combination thereof after contacting a tissue for a length of time. The length of time may be modulated by various factors, as discussed further herein.

In various embodiments, the length of time over which the change in shape and/or hardness occurs may vary from about 1 minute to about 10 days, depending upon the chemical makeup of the surface profile and the environmental conditions to which the surface profile is exposed. Surface profiles changing shape and/or hardness through softening or melting, for example, may occur over the course of about 1 to about 10 minutes during exposure to sufficient thermal conditions. Hydration of a dynamic material to form a gel, in contrast, may occur over the course of about 1 hour to about 48 hours, or even more. Slow dissolution of a sparingly soluble material may occur over a similar or longer time frame. Factors influencing the rate of change of shape and/or hardness in a dynamic material are described hereinbelow for particular dynamic materials. Illustrative time frames over which a change in shape and/or hardness may occur in a dynamic material include, for example, between about 1 to about 5 minutes, or between about 5 minute to about 60 minutes, or between about 60 minutes to about 300 minutes, or between about 6 hours and about 12 hours, or between about 12 hours and about 24 hours, or between about 24 hours and about 48 hours, or between about 48 hours and about 144 hours, or between about 6 hours and about 24 hours, or between about 6 hours and about 48 hours, or between about 6 hours and about 72 hours. A change in shape and/or hardness that occurs over the range of about 6 hours to about 72 hours, or any subrange thereof, may be particularly desirable to promote effective sensor implantation and to impact perfusion proximal to the site of sensor implantation.

In some embodiments, the surface profile may comprise one or more protrusions extending from the base surface. The protrusions may encompass any shape, including the particular protrusion configurations discussed herein. In some embodiments, the surface profile may comprise multiple protrusions, and in other embodiments, a single protrusion may be present. Multiple protrusion configurations may also be present in a single surface profile, according to some embodiments. In still further embodiments, the surface profile may comprise at least one depression or recess in addition to the one or more protrusions. In some or other embodiments, the one or more protrusions may also include at least one concave region upon at least a portion of the protrusions.

In some embodiments, at least a portion of the surface profile may comprise a dynamic material. Incorporation of the dynamic material within the surface profile may allow the change in shape and/or hardness to take place upon exposure to particular conditions during use. The location at which the dynamic material is incorporated within the surface profile is not considered to be particularly limited, provided that the surface profile is able to change in shape and/or hardness once the dynamic material has undergone a change in morphology. Particular locations where the dynamic material may be incorporated within the surface profile are discussed hereinbelow.

Suitable dynamic materials are not considered to be particularly limited. In illustrative embodiments, suitable dynamic materials may include a gel-forming material; a dissolvable material; a material that is thermally deformable or thermally degradable, particularly at or near physiological temperatures; a material that is thermally deformable or thermally degradable above physiological temperatures; a material that is chemically deformable by air, water or light; a hygroscopic material; a suspension-forming material; an elastically deformable material; an inelastically deformable material; a viscoelastic deformable material; a thermoplastic elastomer; and any combination thereof. Particular examples of certain dynamic materials follow hereinafter. Choice of a particular dynamic material may be governed by a number of factors, such as the location where the dynamic material is incorporated in the surface profile, the environmental conditions to which the surface profile may be exposed, and the rate at which the change in morphology of the dynamic material is desired to occur during use.

In some embodiments, the dynamic material within the surface profiles may comprise two or more different dynamic materials in layers, such that the dynamic materials undergo a change in shape and/or hardness at different rates. For example, in particular embodiments, a first/outer dynamic material layer may undergo a change in shape and/or hardness at a faster rate than a second/inner dynamic material layer within a surface profile.

In some embodiments, gel-forming materials may include biological substances or synthetically modified biological substances that may undergo crosslinking to form a gelled state. Suitable biological or synthetically modified biological substances may include, for example, polysaccharides, acetylated polysaccharides, propionylated polysaccharides, cellulose derivatives, gums (e.g., xanthan, guar, diutans, and the like), acetylated guar, starches, derivatized starches, chitosan, chitan, scleroglucans, and the like. In more specific embodiments, suitable gellable substances may include cellulose derivatives such as, for example, methylcellulose, ethylcellulose, hydroxyethylcellulose, hydroxypropylmethylcellulose, carboxymethylcellulose, cellulose esters (e.g., cellulose acetate) and the like. The change in shape and/or hardness of such gellable materials may range from about 1 hour to about 48 hours, or about 6 hours to about 48 hours, or about 12 hours to about 72 hours, depending on particular environmental and physiological conditions to which the surface profile is exposed, such as the local humidity or how much a wearer perspires or bathes. Other factors influencing how quickly moisture reaches the surface profile may likewise impact the rate at which the change of shape and/or hardness occurs. Additional factors potentially influencing the hydration rate for the occurrence of gel formation include, for example, the local pH and temperature, admixture of materials having different hydration rates, variation in the amount of solids within the surface profile, the porosity percentage and morphology (and related surface area) within the surface profile, and the presence or absence of crosslinking within the surface profile. The shape of the surface profile and the surface profile's location upon a wearer's body may similarly impact the rate at which the change in shape and/or hardness takes place.

Synthetic gel-forming materials may also be used in the embodiments of the present disclosure. Suitable synthetic gel-forming materials may include, for example, degradable, water-soluble or hydratable polymers such as, for example, polyglycolic acid, polylactic acid, polylactides, polyacrylamide, polymethacrylamide, polyacrylates, polymethacrylates, polyvinyl alcohol, poly(orthoesters), polyethers, polyesters, polyester amides, polyether amides, polyethylene oxides, polyamides, polyacetals, polyketones, polycarbonates, polyanhydrides, polyurethanes, polyester urethanes, polycarbonate urethanes, polycaprolactone urethanes, any copolymer thereof, and any combination thereof. Specific degradable polymers may include, for example, poly(hydroxy alkanoates), poly(β-hydroxy alkanoates), poly(hydroxybutyrates), poly(O)-hydroxy alkanoates [e.g., poly(β-propiolactone) and poly(ε-caprolactone], poly(alkylene dicarboxylates) [e.g., poly(ethylene succinate) and poly(butylene succinate)], poly(hydroxy ester ethers), poly(anhydrides) [e.g., poly(adipic anhydride), poly(suberic anhydride), poly(sebacic anhydride), poly(dodecanedioic anhydride), poly(maleic anhydride) and poly(benzoic anhydride)], polycarbonates (e.g., trimethylenecarbonate), poly(orthoesters), poly(amino acids), poly(ethylene oxides), poly(etheresters), polyester amides, polyamides, poly(dioxepan-2-one), and polyphosphazenes.

Suitable dissolvable materials, in some embodiments, may include organic or inorganic salts. In some embodiments, the organic or inorganic salts may be sparingly soluble when exposed to the environment to which the surface profile is expected. For example, a sparingly soluble salt may undergo slow dissolution when contacting an aqueous environment, thereby slowing the rate at which the change in morphology occurs. Compressed powders, such as sodium or potassium chloride, calcium sulfate, or calcium phosphate, for example, may similarly undergo slow dissolution during use, according to some embodiments. Illustrative organic salts suitable for use in the embodiments of the present disclosure may include, for example, fatty acid salts, tetraalkylammonium compounds and the like. Illustrative inorganic salts that may be suitable include, for example, $CaCO_3$ and $MgCO_3$. Sparingly soluble organic acid binders, such as stearic acid, may be used similarly in some embodiments.

Neutral dissolvable materials may also be used in some embodiments of the present disclosure. Suitable neutral dissolvable materials may include, for example, dehydrated borates, polyhydroxylated compounds, and the like. Illustrative dehydrated borates can include, for example, anhydrous sodium tetraborate (anhydrous borax) and anhydrous boric acid. These anhydrous borates and others are only slightly soluble upon initial exposure to water but slowly rehydrate over time and become more soluble. As such, these compounds afford surface profiles that may change in shape and/or hardness over the course of several days.

Materials that are thermally deformable or degradable at or near physiological temperatures may also constitute suitable dynamic materials. As used herein, the term "at or near physiological temperatures" refers to a temperature between about 30° C. and about 40° C. (37° C. representing a normal human body temperature). Any material degrading, melting, or having a glass transition temperature within this range may suitably function as a dynamic material. Waxes and some thermoplastic polymers may be suitable materials in this regard.

Materials that are thermally deformable or degradable above physiological temperatures may also constitute suitable dynamic materials. In more specific embodiments, such materials may degrade, melt, or soften at a temperature between about 37° C. and about 50° C., or between about 38° C. and about 48° C., or between about 38° C. and about 45° C. A suitable upper temperature limit for applicability may be dictated by the amount of discomfort an individual can withstand. Techniques for affecting thermal deformation or degradation of such dynamic materials may include, for example, heating pads, heated air, immersing in hot water, and the like. Waxes and thermoplastic polymers having somewhat higher thermal stability compared to those that are thermally deformable or degradable at physiological temperatures may be suitable in this regard.

Materials that are chemically deformable or chemically degradable upon exposure to air, oxygen, water or light are likewise not considered to be particularly limited. Polyglycolides such polyglycolic acid, polylactic acid, and poly-ε-caprolactone may be suitable in this regard.

Suitable suspension-forming materials may be combined in a liquid phase and then undergo molding to form a surface profile. In illustrative embodiments, calcium carbonate (e.g., chalk) may be suspended in water and undergo molding to form a desired surface profile shape. Upon exposing the surface profile to water during contact with a tissue surface, the process can reverse, with the surface profile gradually deconsolidating and changing its initial molded shape.

Suitable elastically deformable, inelastically deformable, and viscoelastic materials may include any material having a desired combination of impact strength, hardness and tensile strength. Various rubber materials can be suitable elastically deformable materials, and plastics can be suitable inelastically deformable materials. Maxwell materials and viscoelastic polymers may be suitable viscoelastic materials.

Suitable thermoplastic elastomers may include any low durometer plastic material that does not substantially deform when under pressure from the base surface against a tissue surface. More specifically, suitable substances may have a hardness less than that of a tissue surface against which the surface profile is applied.

In some embodiments, the surface profile may comprise the dynamic material in an exterior layer upon a core material. That is, in such embodiments, the dynamic material may comprise an outer layer that is positioned to contact a tissue, such as a skin surface, with the core material not contacting the tissue. The core material is not considered to be particularly limited and may be chosen, for example, to convey sufficient mechanical strength for supporting the surface profile. In illustrative embodiments, the core material may include substances such as, for example, a thermoplastic material, a cured resin, a metal, a ceramic, glass, or any combination thereof. In more particular embodiments, at least a portion of the core material may comprise a thermoplastic material, such that the core material may be fabricated during at least a portion of a molding process. Suitable thermoplastic materials that may form the core material include those that may be readily molded such as, for example, polyethylene, polypropylene, polystyrene, styrenic block copolymers, thermoplastic olefins, elastomeric alloys, thermoplastic polyurethanes, thermoplastic co-polyesters, thermoplastic polyamides, vulcanized rubber, polyamides, polycarbonates, and the like.

FIGS. 6A, 6B, 7A and 7B show cross-sectional diagrams of surface profiles incorporating a dynamic material in an exterior layer upon a core material, according to various embodiments of the present disclosure. In each of these surface profiles, the dynamic material is positioned to directly contact a tissue of interest during use. As such, the dynamic material may maintain rigidity during sensor insertion to the tissue and thereafter provide a softer tissue interface once its change in morphology has occurred. Formation of the softer tissue interface may occur over the course of several hours to several days. Additional structural details of these surface profiles is provided hereinbelow. Again, the particular dimensions that are depicted should not be considered limiting.

Each surface profile shown in FIGS. 6A, 6B, 7A and 7B is defined upon an insert that may be positioned in a suitable base surface, thereby allowing interchangeability with a common base surface or housing of a medical device to meet the specific needs of a given application. Any suitable technique may be used for affixing the insert to a base surface, such as adhesive bonding, laser welding, mechanical fastening, press fitting, snap fitting, detents, and the like. Although the surface profiles shown in FIGS. 6A, 6B, 7A and 7B have been depicted as being defined upon an insert configured to be affixed to a base surface, it is also to be recognized that the depicted surface profiles may alternately be fabricated directly upon a base surface without departing from the scope of the present disclosure. Moreover, it is also to be appreciated that the particular surface profile configurations depicted in FIGS. 6A, 6B, 7A and 7B may be readily adapted to any of the other surface profile configurations discussed herein. In one illustrative example, the ring-shaped surface profile of FIG. 5 may be modified to incorporate a dynamic material upon a core material to define the ring-shaped surface profile.

Figure 6B:
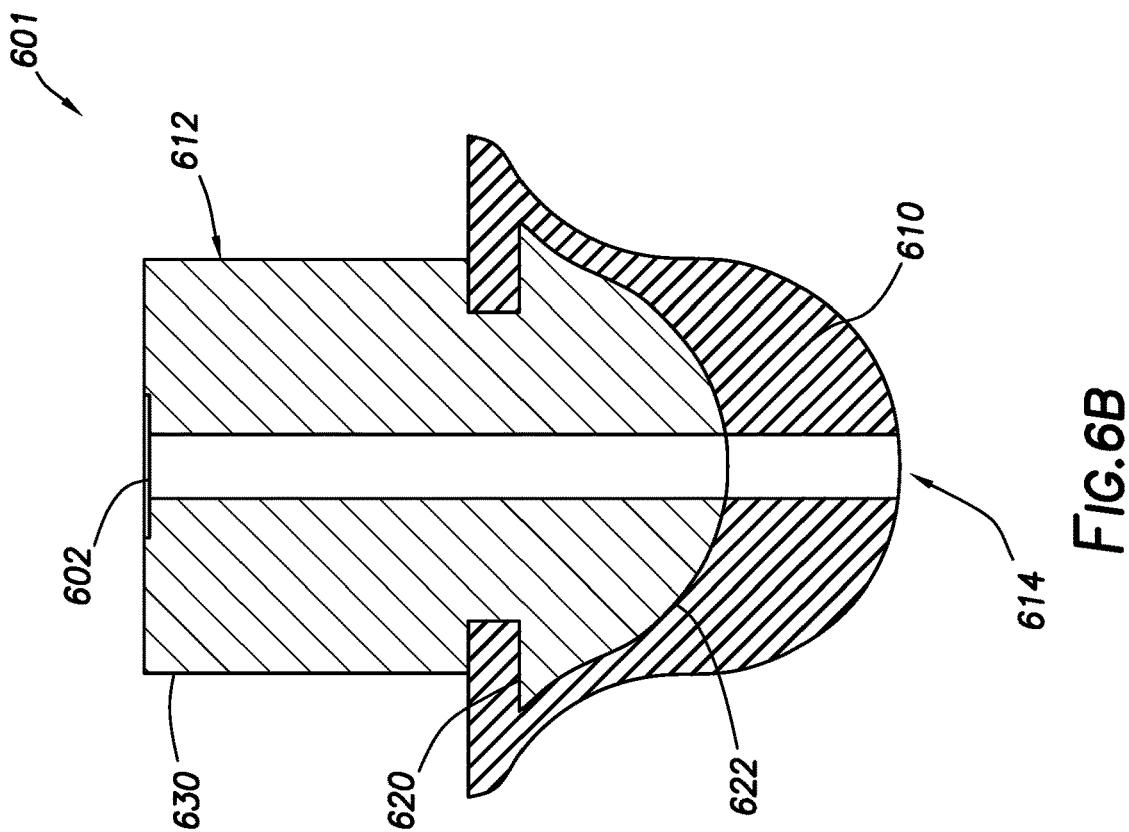
Figure 6A:
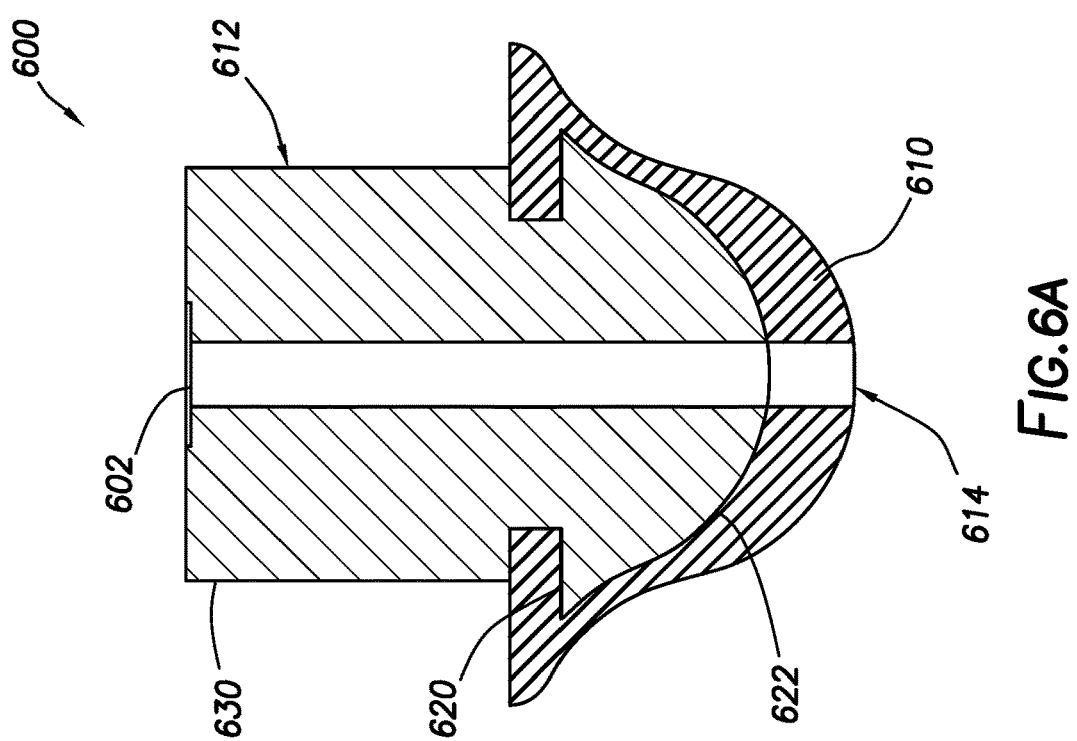

FIGS. 6A and 6B show diagrams of surface profiles 600 and 601, each of which incorporate dynamic material layer 610 upon core material 612. Surface profiles 600 and 601 bear most similarity to surface profile 300 shown in FIG. 3, which has a Gaussian-like cross-section, and may be better understood by reference thereto. Surface profiles 600 and

601 each contain channel 602, within which a suitable sensor (not shown in FIGS. 6A and 6B) may reside. Surface profiles 600 and 601 primarily differ from one another in the thickness of dynamic material layer 610 at distal end 614 of channel 602. The differing thickness of dynamic material layer 610 in surface profiles 600 and 601 may impact the rate and extent to which changes in shape and/or hardness occur when interfaced with a tissue. For example, the change in shape and/or hardness may take longer to occur when the volume of dynamic material layer 610 is larger or when the exposed surface area is smaller.

As further shown in FIGS. 6A and 6B, core material 612 includes lip 620, upon which dynamic material layer 610 may be seated and held in place. Core material 612 also includes curved surface 622, upon which the majority of dynamic material layer 610 resides, specifically the portion positioned to contact a tissue of interest. Neck 630 of core material 612 is not coated with dynamic material layer 610 and is configured for mating and anchoring with a component of a base surface, according to some embodiments. Overbite between lip 620 and neck 630 also aids in interlocking the dynamic material to one or more non-dynamic materials that may be present.

FIGS. 7A and 7B show diagrams of alternative surface profile configurations, which differ from surface profiles 600 and 601 primarily in the shape of core material 612. Namely, in surface profiles 700 and 701 of FIGS. 7A and 7B, core material 612 includes substantially planar surface 720, upon which the majority of dynamic material layer 610 resides. As a result of dynamic material layer 610 residing upon substantially planar surface 720, the distal thickness of dynamic material layer 610 is greater than that in surface profiles 600 and 601 for inserts of otherwise comparable dimensions, which may impact the rate at which the change in shape and/or hardness occurs. Other than the change in shape of core material 612 and the corresponding alteration in distal thickness of dynamic material layer 610, surface profiles 700 and 701 substantially resemble corresponding surface profiles 600 and 601, and similar features are not described in detail again in the interest of brevity. Depending upon the intended application, one may choose a surface profile to having a larger or smaller height, larger or smaller volume of dynamic material, or similar features. Accordingly, the depicted configurations should be considered illustrative in nature and non-limiting.

In alternative configurations, some surface profiles may exclude a core material altogether. When defined as an insert, for example, the surface profile may consist of or consist essentially of a dynamic material, optionally in further combination with one or more substances that are unrelated to changing the shape and/or hardness of the surface profile. That is, in FIGS. 6A, 6B, 7A and 7B, dynamic material 610 may occupy the space of core material 612 to provide a surface profile. Such surface profiles may be compositionally homogenous, as discussed below. Thus, in some embodiments, the dynamic material itself may be shaped for mating with a component of the base surface of a medical device (i.e., as an insert). Likewise, in other embodiments, a surface profile lacking a core material may be defined by shaping a dynamic material upon a component of a base surface of a medical device.

In some or other embodiments, surface profiles, particularly those comprising a protrusion, may be compositionally homogeneous. That is, in such embodiments, surface profiles may lack a compositional disconnect between a dynamic material layer and a core material, such that the dynamic material and any additional admixed components are present throughout the protrusion. When defined as an insert, the dynamic material and any additional admixed components may be configured for mating with a base surface. Compositionally homogenous surface profiles and inserts may bear significant similarity to those described previously hereinabove, except for lacking a compositional disconnect between the dynamic material and a core material, and may be better understood by reference to the preceding disclosure. In some embodiments, compositionally homogenous surface profiles of the foregoing type may comprise an open-cell porous structure, which may optionally leach materials therefrom or receive materials therein as the surface profile changes in shape and/or hardness, as discussed below.

In another configuration, the surface profile may incorporate the dynamic material at least partially enclosed within a shell material, in which the shell material is configured to contact a tissue of interest. More specifically, the shell material may be pliable (deformable) such that it can change shape after the enclosed dynamic material undergoes a change in morphology (i.e., from a first hardness to a second hardness) over a period of time. When the dynamic material is in the first state (harder), the shell material cannot substantially deform, and the surface profile is advantageously rigid to promote sensor insertion. Once the transformation to the second state (softer) occurs, however, the shell material is no longer rigidly held in place by the dynamic material, thereby allowing the surface profile to undergo deformation. Accordingly, in such configurations, the change in morphology of the dynamic material still drives the change in shape and/or hardness of the surface profile, but without requiring the dynamic material to contact a tissue of interest directly. In illustrative embodiments, the shell material may be a thermoplastic elastomer, thereby allowing ready deformation to take place.

Figure 8:
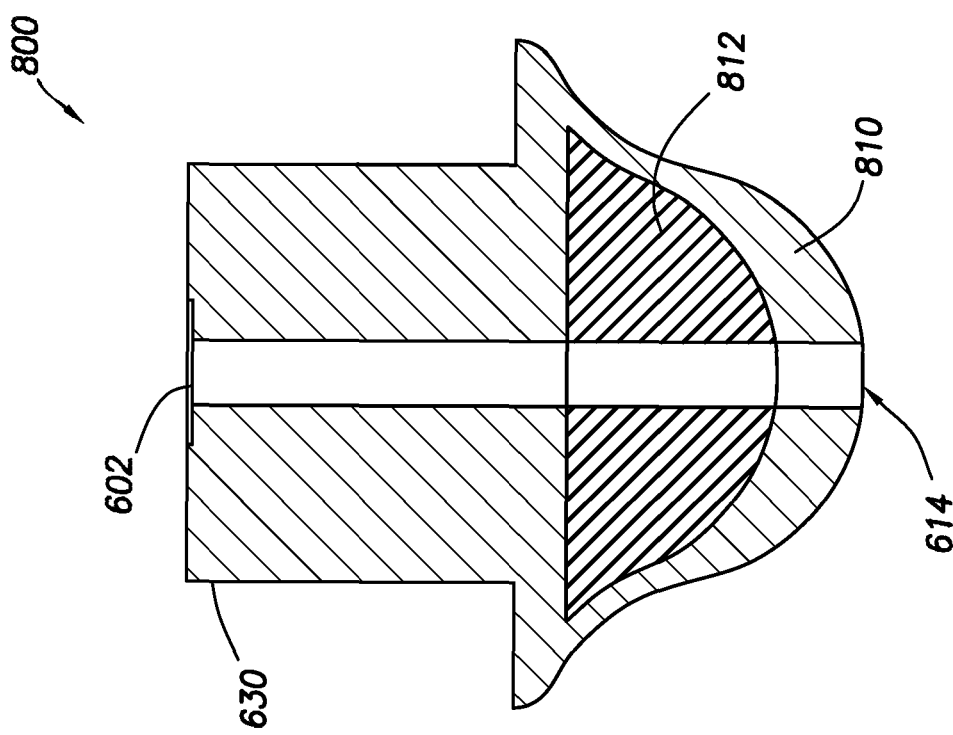
FIG. 8 shows a cross-sectional diagram of a surface profile containing a dynamic material at least partially enclosed within a shell material.

FIG. 8 shows a cross-sectional diagram of a surface profile containing a dynamic material at least partially enclosed within a shell material. As depicted, surface profile 800 includes shell material 810, which defines the exterior of surface profile 800. Dynamic material 812 is contained within the interior of shell material 810. Channel 602 extends from neck 630 through dynamic material 812 and exits through shell material 810 at distal end 614. In the depicted configuration, dynamic material 812 is in communication with its external environment via channel 602. As such, even though dynamic material 812 located within the interior of shell material 810, it may still interact with external stimuli that may promote a change in morphology. Alternately, dynamic material 812 may be fully enclosed within shell material 810, in which case the change in morphology may be promoted without requiring access to dynamic material 812 (e.g., using heat, light, an internal degradant or reactant, or the like). Once the morphology of dynamic material 812 has changed, such as by softening, surface profile 800 as a whole may alter its shape and hardness through deformation of shell material 810.

In still another configuration, surface profiles of the present disclosure may comprise a plurality of struts disposed around the outer surface of an interior material. The struts incompletely surround the interior material, like a cage, and may aid in constraining the surface profile in a particular shape. According to some embodiments, the interior material may comprise an open-cell sponge structure or similar porous construct. In some embodiments, the struts may comprise a dynamic material and the interior material may comprise a pliable substance. When the struts undergo a change in shape or hardness, the interior material can then undergo a corresponding change in shape, such as conforming to a tissue surface. In other embodiments, the struts may comprise a non-dynamic material and the interior material may comprise a dynamic material. Once a change in shape or hardness of the interior material occurs, a corresponding change in the exterior shape may occur due to deformation of the struts. In either configuration, a substance of interest may be released from the interior material once the change in shape occurs, such as the illustrative materials discussed below.

In some embodiments, a drug substance or other biologically active material may be co-present with the dynamic material in any of the surface profiles disclosed herein. In some embodiments, the drug substance or biologically active material may be released before a change in morphology of the dynamic material occurs. In other embodiments, the drug substance or biologically active material may be released after a change in morphology of the dynamic material has occurred and the surface profile has changed in shape and/or hardness. Thus, in some embodiments, surface profiles of the present disclosure may be configured to release a drug substance or biologically active material to a site of sensor implantation, either before or after a change in morphology of the dynamic material has occurred. Suitable drug substances that may be present in the surface profile are not considered to be particularly limited. Suitable biologically active materials are likewise not considered to be particularly limited and may include substances such as biological materials, as well as passive therapeutic substances such as lotions, creams, and the like. In particular embodiments, suitable drug substances or biologically active materials may include, for example, antibiotics, analgesics, anti-inflammatories, nicotine, hormones, essential oils, moisturizers, drugs susceptible to degradation in stomach or those not hemacompatible, insulin, anesthetics, chemotherapeutic agents, vasodilators, nutrients, vitamins, anti-hypertensive vasodilator medication growth factors, and the like.

Sensors incorporated within the medical devices of the present disclosure may be adapted for insertion to any tissue of interest. In illustrative embodiments, the sensor may be adapted for intravenous insertion, subcutaneous insertion, epidermal insertion or dermal insertion. In more particular embodiments, the sensor may be a dermal sensor, and the surface profile may be configured to contact a skin surface for sensor implantation. In such embodiments, an insertion needle or similar introducer may extend from the base surface in proximity to the dermal sensor in order to facilitate sensor insertion into the dermal layer. Analytes that may be detected using the implanted sensor are not particularly limited. In illustrative embodiments, the implanted sensor may be adapted to analyze for glucose, particularly in dermal fluid. In other illustrative embodiments, the sensors may be adapted to conduct passive measurements on one or more fluids upon the exterior of a body, such as tears, aqueous humor, urine, mucus, spit, sweat, urine, ear wax, or fecal matter.

Although the foregoing disclosure is primarily directed to dynamic materials that undergo softening during use, it is also to be recognized that dynamic materials capable of undergoing hardening may be used in a related manner. Dynamic materials that undergo hardening may be particularly advantageous in instances wherein contact with very delicate tissues occurs and tissue damage may otherwise be prevalent.

Methods for fabricating the surface profiles disclosed herein are also contemplated by various embodiments of the present disclosure. In more specific embodiments, methods for fabricating a surface profile may comprise: forming a tissue-facing surface profile upon a base surface, and extending a sensor through the base surface and at least a portion of the tissue-facing surface profile. The tissue-facing surface profile may deviate from the base surface, such as a deviation from planarity, and be configured to undergo a change in shape, hardness, or a combination thereof after contacting a tissue for a length of time.

In some embodiments, the surface profile may be defined upon an insert. As such, in some embodiments, forming the surface profile may comprise defining a protrusion or similar feature upon an insert, and positioning the insert upon a base surface. Any of the surface profiles disclosed herein may be fabricated in this manner. Alternately, the surface profile may be fabricated directly on the base surface without first being defined upon an insert.

In more specific embodiments, surface profiles containing a dynamic material layer external to a core material may be fabricated by a molding process. In a first operation, the core material may be fabricated in a desired shape using a first mold. Thereafter, the core material may be transferred to a second mold and the dynamic material may be overmolded onto the core material. In some embodiments, the surface profile may then be freeze dried (lyophilized) to remove solvent from the dynamic material and form a solid dynamic material layer upon the core material. Surface profiles excluding a core material may be fabricated by a similar molding process using a single mold.

Surface profiles including a dynamic material within a shell material may be fabricated by a related process. In order to fabricate such surface profiles, the shell material may be fabricated by a suitable molding process to define an internal recess suitable for receiving the dynamic material. The dynamic material may then be introduced into the recess and freeze dried in a manner similar to that described above for defining an external dynamic material layer.

The sensor may be extended through the surface profile and the base surface either after fabrication of the surface profile or during fabrication of the surface profile. In some embodiments, the above fabrication steps may be conducted by inserting the sensor into a suitable recess in the mold and fabricating the surface profile around the sensor. In other embodiments, the above fabrication steps may be conducted to define a solid workpiece, and then a channel suitable to receive the sensor may be milled as a final operation before inserting the sensor. Any combination of machining (including milling) and molding may be used to define the dynamic material and the core material (when present) into a desired shape.

In still other various embodiments, the present disclosure provides methods for using a medical device containing a surface profile configured to change in shape and/or hardness during use. In more specific embodiments, such methods of the present disclosure may comprise: providing a medical device comprising a base surface having a tissue-facing surface profile defined thereon, and a dermal sensor extending through the base surface and at least a portion of the tissue-facing surface profile, the tissue-facing surface profile comprising a protrusion extending from the base surface; and positioning the tissue-facing surface profile against a skin surface such that the dermal sensor becomes inserted at a first depth in a dermal layer below the skin surface. At least one of a change in shape or a change in hardness occurs after contacting the tissue-facing surface profile against the skin surface.

After contacting the skin surface and a change in shape and/or hardness occurs within the dynamic material, the dermal sensor may become inserted at a second depth in the dermal layer. In more specific embodiments, the second depth may be greater than the first depth. As such, the surface profiles of the present disclosure may facilitate more secure implantation of the sensors and lessen the likelihood or sensor pullout during use.

Embodiments disclosed herein include:

A. Medical devices for assaying an analyte. The medical devices comprise: a base surface having a tissue-facing surface profile defined thereon, the tissue-facing surface profile deviating from the base surface; and a sensor extending through the base surface and at least a portion of the tissue-facing surface profile; wherein the tissue-facing surface profile is configured to undergo a change in shape, hardness, or a combination thereof after contacting a tissue for a length of time.

B. Methods for forming a surface profile. The methods comprise: forming a tissue-facing surface profile upon a base surface, the tissue-facing surface profile deviating from the base surface and being configured to undergo a change in shape, hardness, or a combination thereof after contacting a tissue for a length of time; and extending a sensor through the base surface and at least a portion of the tissue-facing surface profile.

C. Methods for contacting a surface profile with a tissue. The methods comprise: providing a medical device comprising a base surface having a tissue-facing surface profile defined thereon, and a dermal sensor extending through the base surface and at least a portion of the tissue-facing surface profile, the tissue-facing surface profile comprising a protrusion extending from the base surface; and positioning the tissue-facing surface profile against a skin surface such that the dermal sensor becomes inserted at a first depth in a dermal layer below the skin surface; wherein at least one of a change in shape or a change in hardness occurs after contacting the tissue-facing surface profile against the skin surface.

Each of embodiments A, B, and C may have one or more of the following additional elements in any combination Element 1: wherein the tissue-facing surface profile comprises a protrusion extending from the base surface.

Element 2: wherein at least a portion of the protrusion is defined upon an insert positioned in the base surface.

Element 3: wherein the protrusion comprises a dynamic material in an exterior layer upon a core material, the dynamic material being positioned to contact the tissue.

Element 4: wherein the protrusion comprises a dynamic material that is positioned to contact the tissue.

Element 5: wherein the protrusion is compositionally homogenous.

Element 6: wherein the protrusion comprises a dynamic material at least partially enclosed within a shell material, the shell material being pliable and positioned to contact the tissue.

Element 7: wherein at least a portion of the protrusion comprises a dynamic material, the dynamic material being positioned to contact the tissue.

Element 8: wherein the dynamic material comprises at least one substance selected from the group consisting of a gel-forming material; a dissolvable material; a material that is thermally deformable or thermally degradable at or near physiological temperatures; a material that is thermally deformable or thermally degradable above physiological temperatures; a material that is chemically deformable or chemically degradable by air, water or light; a hygroscopic material; a suspension-forming material; an elastically deformable material; an inelastically deformable material; a viscoelastic deformable material; a thermoplastic elastomer; and any combination thereof.

Element 9: wherein at least a portion of the tissue-facing surface profile comprises a dynamic material.

Element 10: wherein the tissue-facing surface profile is configured to decrease in hardness after contacting the tissue.

Element 11: wherein the medical device further comprises: a drug substance or biologically active material disposed upon or within the tissue-facing surface profile, the drug substance or biologically active material being releasable from the tissue-facing surface profile upon the tissue-facing surface profile undergoing the change in shape, hardness, or combination thereof.

Element 12: wherein the sensor is a dermal sensor and the tissue is a skin surface, the medical device further comprising: an introducer extending from the base surface in proximity to the dermal sensor.

Element 13: wherein forming the tissue-facing surface profile comprises defining a protrusion upon an insert, and positioning the insert upon the base surface, at least a portion of the protrusion comprising the dynamic material.

Element 14: wherein the dermal sensor becomes inserted at a second depth in the dermal layer after at least one of the change in shape or the change in hardness occurs.

By way of non-limiting example, exemplary combinations applicable to A, B, and C include:

The medical device of A or the method of B in combination with elements 1 and 2; 1 and 4; 1 and 5; 1 and 6; 1 and 10; 1 and 11; 1 and 12; 1, 2 and 3; 1, 2 and 4; 1, 2 and 5; 1, 2 and 6; 1, 2 and 8; 1 and 7; 8 and 9; 9 and 10; 8, 9 and 10; 8, 9 and 11; 8, 9, 10 and 12; 10 and 11; 10 and 12; and 11 and 12.

The method of B in combination with elements 8 and 13; elements 1, 2 and 13; 1, 4 and 13; 1, 5 and 13; 1, 6 and 13; 1, 10 and 13; 1, 11 and 13; 1, 12 and 13; 1, 2, 3 and 13; 1, 2, 4 and 3; 1, 2, 5 and 3; 1, 2, 6 and 13; 1, 2, 8 and 13; 1, 7 and 13; 8, 9 and 13; 9, 10 and 13; 8, 9, 10 and 13; 8, 9, 11 and 13; 8, 9, 10, 12 and 13; 10, 11 and 13; 10, 12 and 13; and 11, 12 and 13.

The method of C in combination with elements 2 and 3; 2 and 4; 2 and 5; 2 and 6; 2, 3 and 8; 2, 4 and 8; 2, 6 and 8; 2 and 10; 2 and 11; 2 and 12; 3 and 8; 4 and 5; 4 and 8; 6 and 8; 3 and 10; 4 and 10; 5 and 10; 6 and 10; 10 and 11; 10 and 12; 8 and 14; 2, 3 and 14; 2, 4 and 14; 2, 5 and 14; 2, 6 and 14; 2, 3, 8 and 14; 2, 4, 8 and 14; 2, 6, 8 and 14; 2, 10 and 14; 2, 11 and 14; 2, 12 and 14; 3, 8 and 14; 4, 5 and 14; 4, 8 and 14; 6, 8 and 14; 3, 10 and 14; 4, 10 and 14; and 5, 10 and 14.

To facilitate a better understanding of the embodiments described herein, the following examples of various representative embodiments are given. In no way should the following examples be read to limit, or to define, the scope of the disclosure.

EXAMPLES

Figure 9:
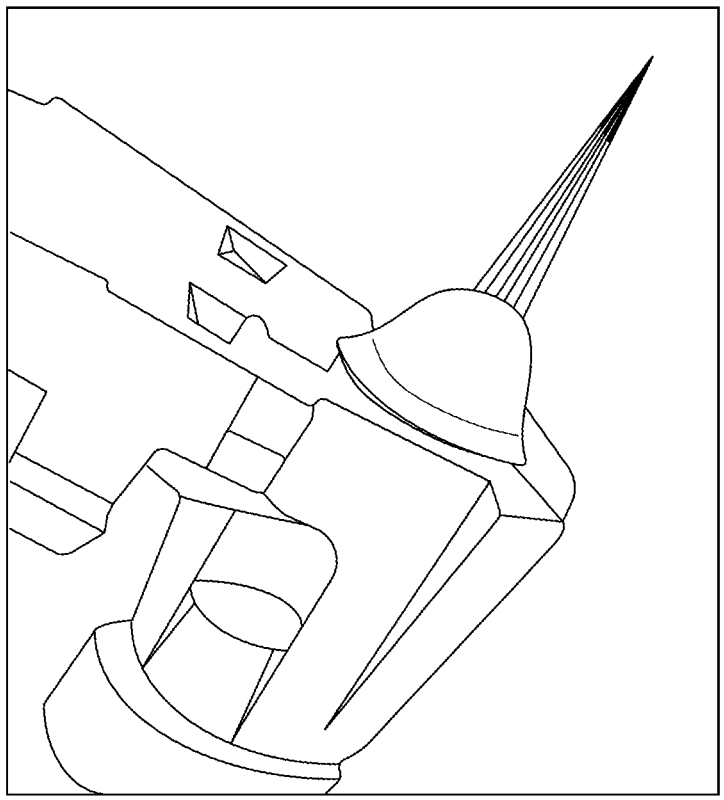
FIGS. 9 and 10 show photographs of a surface profile mounted to a base surface and fitted with a sensor and an insertion needle before and after dynamic material hydration, respectively.
Figure 10:
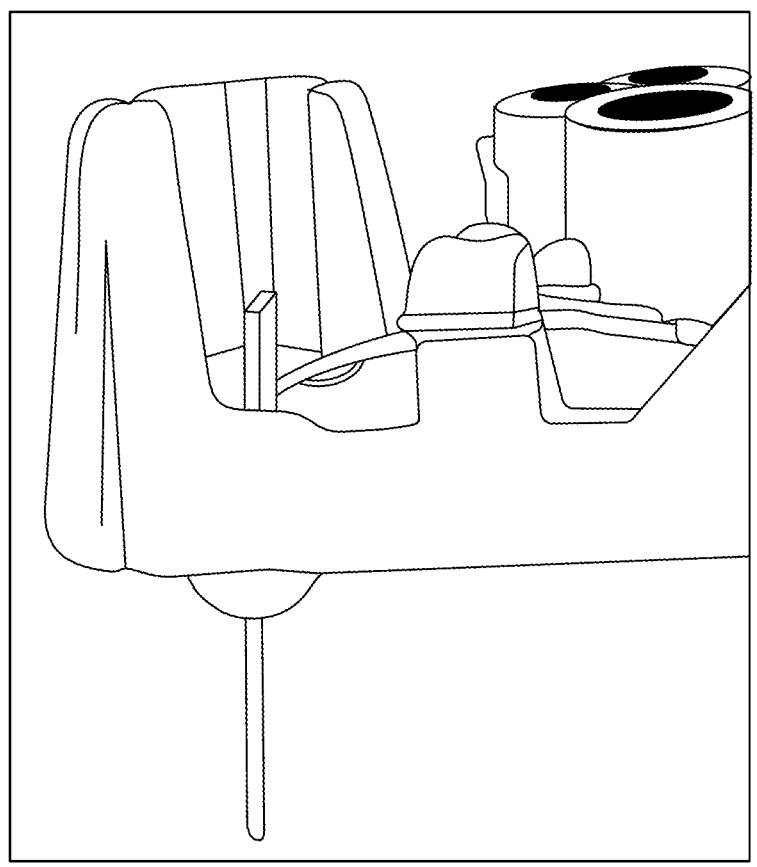

An insert similar to that shown in FIG. 7A was prepared by a two-step molding process. A thermoplastic core was first prepared by injection molding. The mold was partially disassembled and then reassembled with a new cavity surrounding the core. Thereafter, a 25 wt. % hydroxypropyl-methylcellulose (HPMC) solution was gently applied via syringe to the new cavity. Freeze drying (lyophilization) was then conducted to remove the solvent, thereby overmolding the hydroxypropylmethylcellulose onto the thermoplastic core. Following freeze drying, the finished insert was removed and fitted with a sensor and insertion needle in a transponder plug. FIGS. 9 and 10 show photographs of the surface profile mounted to a base surface and fitted with a sensor and insertion needle before and after dynamic material hydration and induced collapse and gelling, respectively. As shown, the hydroxypropylmethylcellulose softened and contracted upon hydration, thereby increasing the exposed length of the sensor available for implantation. For example, prior to hydration of the dynamic material, the sensor tail was exposed approximately 2.0 mm, and after hydration, approximately 3.45 mm was exposed.

Figure 11:
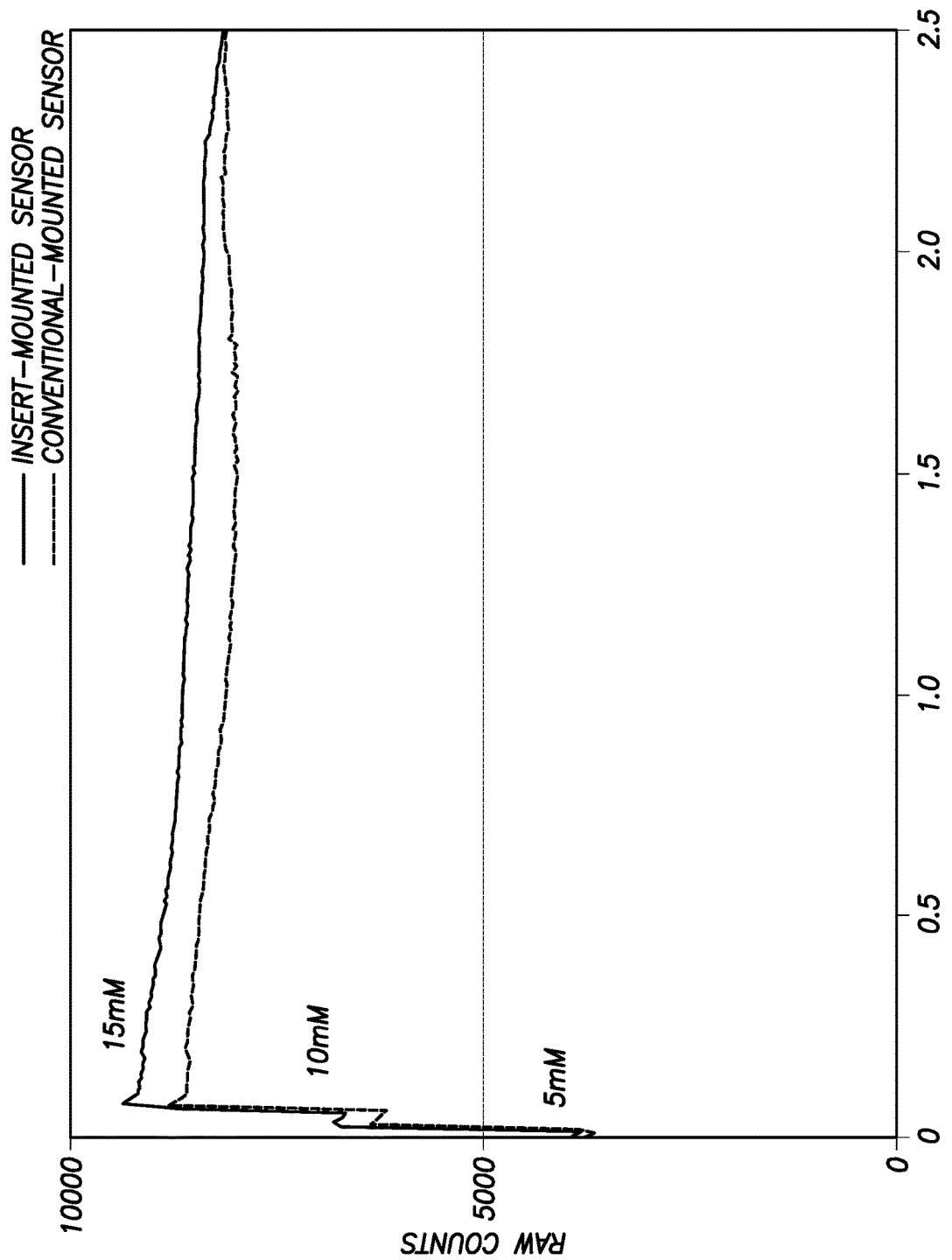
FIG. 11 shows a graph of illustrative sensor response for a conventionally mounted sensor against that of a sensor mounted within a surface profile incorporating a dynamic material.

The mounted sensor was also tested in vitro for assaying a 5-15 mM glucose solution in 100 mm phosphate buffered saline. FIG. 11 shows a graph of illustrative sensor response for a conventionally mounted sensor against that of a sensor mounted within a surface profile containing a dynamic material. As shown, the surface profile did not significantly alter the sensor response.

Unless otherwise indicated, all numbers expressing quantities and the like in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating various features are presented herein. Not all features of a physical implementation are described or shown in this application for the sake of clarity. It is understood that in the development of a physical embodiment incorporating the embodiments of the present disclosure, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While various systems, tools and methods are described herein in terms of "comprising" various components or steps, the systems, tools and methods can also "consist essentially of" or "consist of" the various components and steps.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Therefore, the disclosed systems, tools and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems, tools and methods illustratively disclosed herein may suitably be practiced in the absence of any element that is not specifically disclosed herein and/or any optional element disclosed herein. While systems, tools and methods are described in terms of "comprising," "containing," or "including" various components or steps, the systems, tools and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

What is claimed is the following:

1. A medical device for assaying an analyte, the medical device comprising:
    a sensor housing comprising a base surface having a tissue-facing surface profile defined thereon, the tissue-facing surface profile comprising a core extending from the base surface, wherein the core comprises a core material, and a protrusion disposed on a tip of the core and having a convex surface, wherein the protrusion comprises a dynamic material that is different than the core material, wherein the dynamic material has a first hardness configured to transition to a second hardness that is lower than the first hardness over a period of time in which the medial device is in use, and wherein the tissue-facing surface profile is configured to be placed against a skin surface of a user; and
    an analyte sensor at least partially arranged within the sensor housing, wherein a portion of the analyte sensor extends through the base surface, the core and the protrusion, wherein the portion of the analyte sensor is configured to be positioned under the skin surface and in contact with a biological fluid of the user.

2. The medical device of claim 1, wherein the protrusion is at least partially enclosed within a shell material, the shell material being pliable and positioned to contact the skin surface of the user.

3. The medical device of claim 1, wherein the dynamic material comprises a dissolvable material; a material that is thermally degradable at or near physiological temperatures; a material that is thermally degradable above physiological temperatures; a material that is chemically degradable by air, water, or light; a degradable gel-forming material; or any combination thereof.

4. The medical device 1, further comprising:
a drug substance or biologically active material disposed upon or within the tissue-facing surface profile, the drug substance or biologically active material being releasable from the tissue-facing surface profile upon the tissue-facing surface profile undergoing a change in hardness.

5. The medical device of claim 1, wherein the sensor is a dermal sensor, the medical device further comprising:
an introducer extending from the base surface in proximity to the dermal sensor to promote introduction of the dermal sensor into the skin surface.

6. The medical device of claim 1, wherein the period of time is about one (1) minute to about ten (10) days.

7. The medical device of claim 6, wherein the period of time is about six (6) hours to about seventy-two (72) hours.

8. The medical device of claim 1, wherein the dynamic material comprises a material that is thermally degradable at, near, or above physiological temperatures.

9. The medical device of claim 1, wherein the dynamic material comprises a material that is chemically degradable by air, water, or light.

10. The medical device of claim 1, wherein the protrusion comprises a hemispherical shape.

11. The medical device of claim 1, wherein the protrusion comprises a planar face, and wherein the analyte sensor extends through the planar face of the protrusion.

12. The medical device of claim 1, wherein the protrusion is one of a plurality of protrusions of the tissue-facing surface profile.

13. A medical device for assaying an analyte, the medical device comprising:
a sensor housing comprising a base surface having a tissue-facing surface profile defined thereon, the tissue-facing surface profile comprising a protrusion having a convex surface extending from the base surface; and
an analyte sensor at least partially arranged within the sensor housing, wherein a portion of the analyte sensor extends through the base surface and at least a portion of the tissue-facing surface profile, wherein the portion of the analyte sensor is configured to be positioned under the skin surface and in contact with a biological fluid of the user,
wherein the tissue-facing surface profile further comprises a core comprising a core material and the protrusion disposed on a tip of the core, wherein the protrusion comprises a dynamic material that is different than the core material, the dynamic material comprising a first hardness to facilitate insertion of the analyte sensor under the skin surface, and wherein the dynamic material is configured to transition to a second hardness that is lower than the first hardness when exposed to moisture.

14. The medical device of claim 13, wherein the dynamic material comprises a gel-forming material.

15. The medical device of claim 13, wherein the dynamic material comprises a cellulose derivative.

16. A medical device for assaying an analyte, the medical device comprising:
a sensor housing comprising a base surface having a tissue-facing surface profile defined thereon, the tissue-facing surface profile configured to be placed against a skin surface of a user; and
an analyte sensor at least partially arranged within the sensor housing, wherein a portion of the analyte sensor extends through the base surface and at least a portion of the tissue-facing surface profile, wherein the portion of the analyte sensor is configured for insertion into the tissue and in contact with a biological fluid of the user;
wherein the protrusion of the tissue-facing surface profile comprises:
a core extending from the base surface, wherein the core comprises a core material; and
a protrusion disposed on a tip of the core and defining a convex surface, wherein the protrusion comprises a dynamic material that is different from the core material, and wherein the dynamic material has a first hardness configured to facilitate insertion of the analyte sensor into the tissue, wherein the dynamic material is configured to transition to a second hardness that is lower than the first hardness over a period of time in which the medical device is in use.

17. The medical device of claim 16, wherein the core material comprises a thermoplastic material.

18. The medical device of claim 16, wherein the core comprises a neck and a lip, wherein the dynamic material is disposed on the lip of the core material.

19. The medial device of claim 16, wherein the analyte sensors extends through a channel formed in the core and the protrusion of the tissue-facing surface profile.

* * * * *